United States Patent [19]

Jansen et al.

[11] Patent Number: 5,147,387
[45] Date of Patent: Sep. 15, 1992

[54] PROCESS OF IMPLANTING A PROSTHETIC SHEET REPAIR MATERIAL

[75] Inventors: David W. Jansen; Thomas M. O'Hara, both of Flagstaff, Ariz.

[73] Assignee: W. L. Gore & Associates, Inc., Newark, Del.

[21] Appl. No.: 803,651

[22] Filed: Oct. 11, 1991

Related U.S. Application Data

[63] Continuation of Ser. No. 598,465, Oct. 10, 1990, abandoned.

[51] Int. Cl.$^5$ .............................................. A61F 2/06
[52] U.S. Cl. ............................................. 623/1; 623/11
[58] Field of Search ............................. 623/1, 11, 12

[56] References Cited

U.S. PATENT DOCUMENTS

| | | |
|---|---|---|
| 4,291,694 | 9/1981 | Chai . |
| 4,740,207 | 4/1988 | Kreamer ................................ 623/1 |
| 4,811,743 | 3/1989 | Stevens ............................... 128/772 |
| 4,877,030 | 10/1989 | Beck et al. .............................. 623/1 |
| 4,923,464 | 5/1990 | DiPisa, Jr. ............................ 623/11 |
| 4,971,490 | 11/1990 | Hawkins ............................. 128/772 |
| 5,007,895 | 4/1991 | Burnett . |
| 5,059,211 | 10/1991 | Stack et al. ............................. 623/1 |

FOREIGN PATENT DOCUMENTS

| | | |
|---|---|---|
| 3217006 | 11/1983 | Fed. Rep. of Germany . |
| 8900439 | 3/1989 | Fed. Rep. of Germany . |

Primary Examiner—Randy C. Shay
Attorney, Agent, or Firm—Wayne D. House

[57] ABSTRACT

A surgical instrument for use in laparoscopy surgeries, useful for implanting prosthetic sheet repair materials when surgical repair of body membranes or wall structures is required. The use of the inventive surgical instrument minimizes the length of incision required to implant a piece of prosthetic sheet repair material.

8 Claims, 6 Drawing Sheets

PROCESS OF IMPLANTING A PROSTHETIC SHEET REPAIR MATERIAL

This application is a continuation of application Ser. NO. 07/598,465 filed on Oct. 10, 1990 for a LAPAROSCOPY SURGICAL INSTRUMENT, now abandoned.

FIELD OF THE INVENTION

This invention relates to the field of surgical instruments, and in particular to a surgical instrument for use in laparoscopy surgeries to implant prosthetic sheet repair materials when surgical repair of body membranes is required.

BACKGROUND OF THE INVENTION

The repair of weak or damaged body membranes or wall structures, for example hernia repairs, peritoneal and pericardial repairs, is a well known surgical art. Such repairs are typically made through incisions large enough to allow the surgeon access to the defective membrane with his hands. Repair of the defective membrane or wall structure often requires the use of additional material in the form of prosthetic sheet repair materials to reinforce the defective tissue. These materials are typically in the form of porous flat sheets or sheets of mesh having visibly open spaces between the components of the mesh. They are usually made of biocompatible polymers such as polytetrafluoroethylene, polyethylene terephthalate or polypropylene; alternatively they may be made of bioabsorbable materials such as oxidized regenerated cellulose, polyglycolic acid, polylactic acid or copolymers thereof. The repair is typically accomplished by suturing the perimeter of the prosthetic sheet repair material to the body membrane in such a manner that the defective portion of the body membrane is covered by the prosthetic sheet repair material. The mechanical stresses normally carried by the body membrane or wall structure are largely transferred to the sheet of prosthetic repair material and to the sutures or other surgical fasteners used to retain that material in place. It is apparent that an incision adequate to allow access by a surgeon's hands so that the prosthetic sheet repair material may be properly sutured into place will have to be of substantial length. The resulting surgical trauma and time required for healing are also substantial.

SUMMARY OF THE INVENTION

This invention relates to a surgical instrument for use in implanting prosthetic sheet repair materials for the repair of defective body membranes or wall structures via incisions of reduced length. The inventive surgical instrument comprises in its simplest embodiment a length of rod having an outside diameter and first and second ends, wherein said rod has adjacent to the first end a short length of reduced outside diameter in comparison to the rod outside diameter. A sheet of prosthetic repair material may be wrapped around the portion of the rod having the short length of reduced diameter, then inserted through a trocar sleeve previously placed into the appropriate body cavity via a small incision, to a position in close proximity to the defective body membrane or wall structure requiring repair. By rotating the rod in the direction appropriate to cause the rolled-up prosthetic sheet material to unroll, the prosthetic sheet material is presented to the site requiring repair. Forceps may be used to aid in unrolling the prosthetic sheet repair material from the rod. The tip of the inventive surgical instrument may be used to maneuver the sheet of prosthetic repair material as necessary into place over the defect site. The prosthetic sheet repair material may be fastened into place over the defect site by the use of various types of surgical fasteners, for example, as described in U.S. Pat. No. 4,873,976. Other embodiments of the present invention include the use of a flexible shaft or handle portion and an embodiment wherein the shaft or handle portion is separately rotatable from the reduced diameter portion. The shaft or handle portion may also be made to be removable from the reduced diameter portion; the reduced diameter portion may incorporate a slot through its diameter.

DETAILED DESCRIPTION OF THE INVENTION

Figure 1:
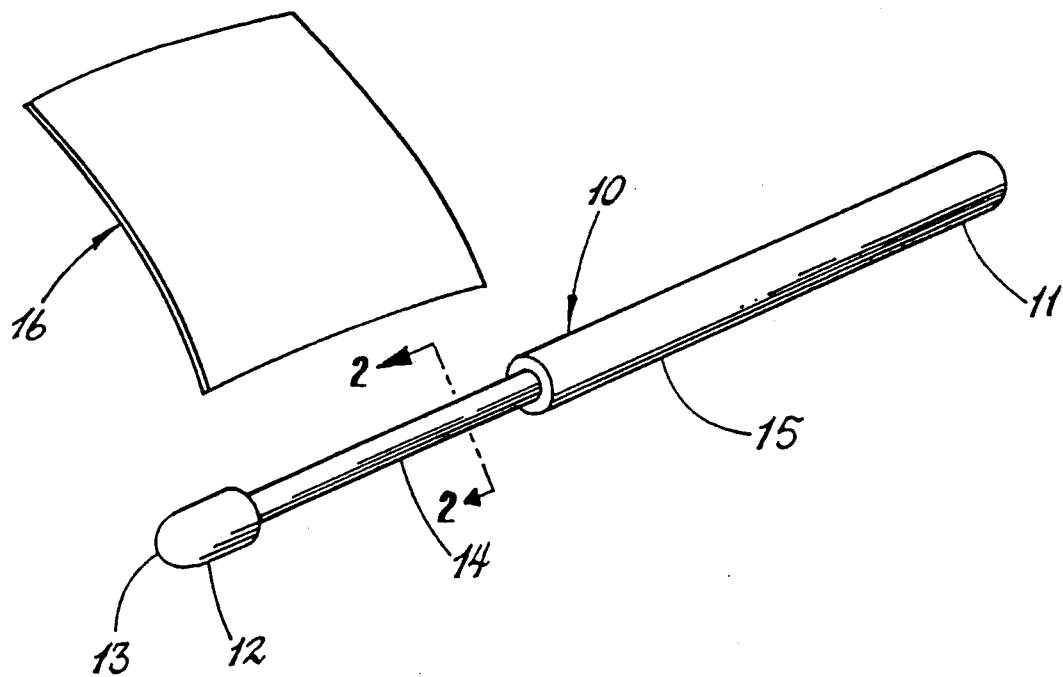
FIG. 1 shows a perspective view of the surgical instrument of the present invention and a sheet of prosthetic repair material for use with the surgical instrument.

As shown by the perspective view of FIG. 1, the surgical instrument 10 of the present invention comprises a length of rod having a second end 11 and a first end 12 having a portion 14 of said length with a reduced diameter adjacent to the first end 12. The tip of the instrument 10 is radiused to allow smooth entry via an incision into the body cavity. For convenience, the remaining length of the rod-like instrument 10 will be referred to as the shaft. A piece of prosthetic sheet repair material 16 is shown adjacent to the reduced diameter portion 14 of the instrument 10 in position to be rolled up around the reduced diameter portion 14.

Figure 2:
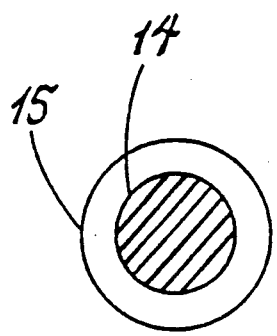
FIG. 2 shows a cross section of the reduced diameter portion of the surgical instrument of the present invention

FIG. 2 shows the round cross section, taken at A—A', of the cylindrical form of the reduced diameter portion 14.

Figure 3:
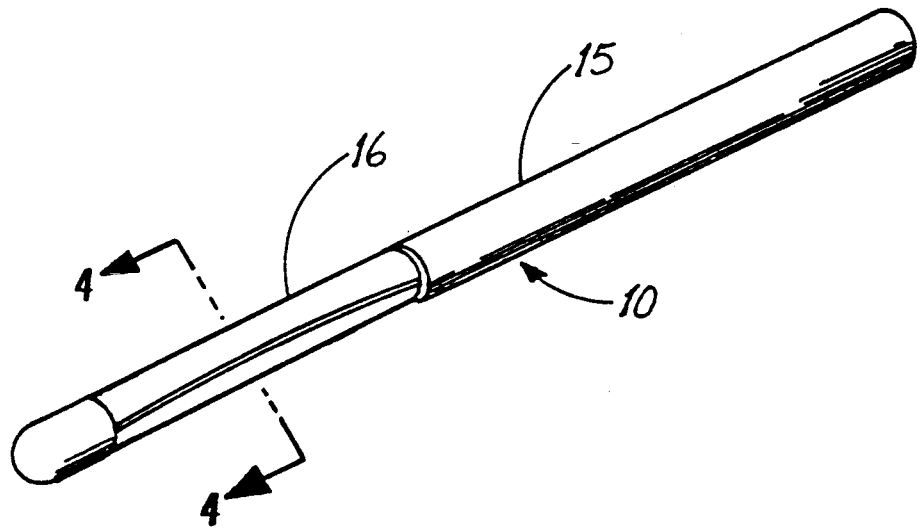
FIG. 3 shows a perspective view of the surgical instrument of the present invention during surgical use wherein a sheet of prosthetic repair material is shown wrapped around the reduced diameter portion of the instrument.
Figure 4:
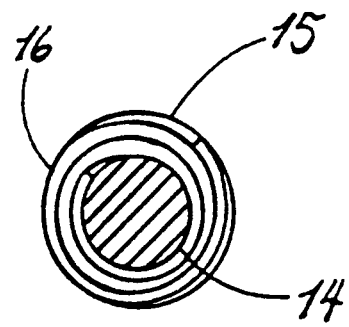
FIG. 4 shows a cross section of the reduced diameter portion of the surgical instrument of the present invention during surgical use wherein a sheet of prosthetic repair material is shown wrapped around the reduced diameter portion of the instrument.

FIG. 3 describes the appearance of the instrument 10 during use at which time the piece of prosthetic sheet repair material 16 is rolled up around the reduced diameter portion 14. The same appearance is shown in the cross section of FIG. 4 taken at B—B'.

Figure 5:
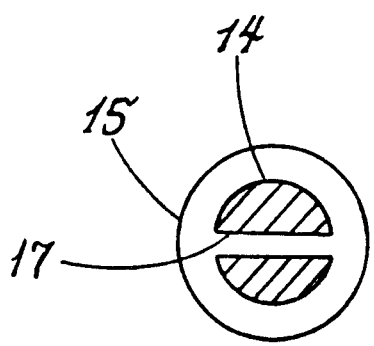
FIG. 5 shows a cross section of the reduced diameter portion of an alternative embodiment of the surgical instrument wherein a slot exists through the length of the reduced diameter portion.
Figure 6:
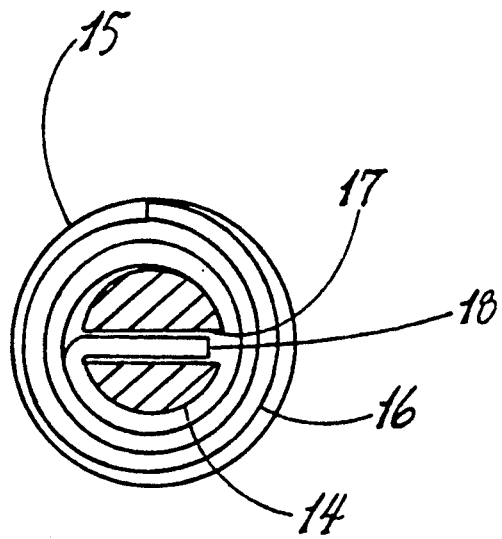
FIG. 6 shows the cross section of the surgical instrument of FIG. 5 in use, wherein a sheet of prosthetic repair material is shown wrapped around the reduced diameter portion of the instrument with one edge of the prosthetic sheet inserted through the slot in the instrument.

An alternative embodiment is described in the cross section of FIG. 5 wherein the reduced diameter portion has a slot 17 cut through the reduced diameter portion 14 for the entire length of that portion. The slot 17 is typically centered over a diameter of the reduced diameter portion 14 and is of width slightly greater than the thickness of the prosthetic repair material. As shown by FIG. 6, an edge 18 of the prosthetic sheet repair material 16 may be inserted into the slot 17 prior to rolling the repair material around the reduced diameter portion 14 of the instrument. A piece of prosthetic sheet repair material 16 is shown in the cross section of FIG. 6, wherein the sheet is shown rolled-up around the reduced diameter portion 14 of the surgical instrument of this embodiment with one edge 18 of the prosthetic sheet material 16 inserted through the slot 17 in the instrument.

Figure 7:
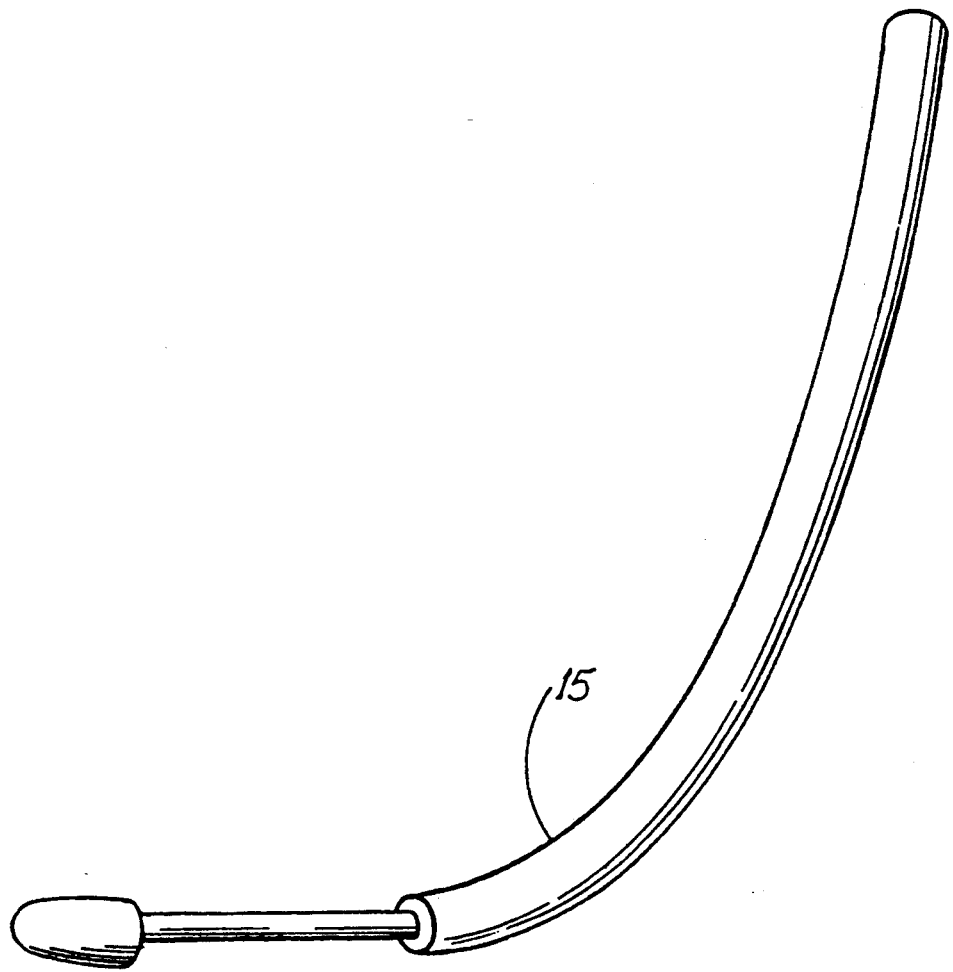
FIG. 7 shows a perspective view of one embodiment of the surgical instrument wherein the shaft portion of the instrument is a flexible shaft.

FIG. 7 shows another alternative embodiment wherein the shaft portion 15 adjacent to the second end of the instrument comprises a flexible shaft. By flexible is meant that the shaft is bendable or incorporates a swivel to allow the instrument to be used with the handle or shaft portion set at an angle to the reduced diameter portion. This may be advantageous for certain applications.

Figure 8:
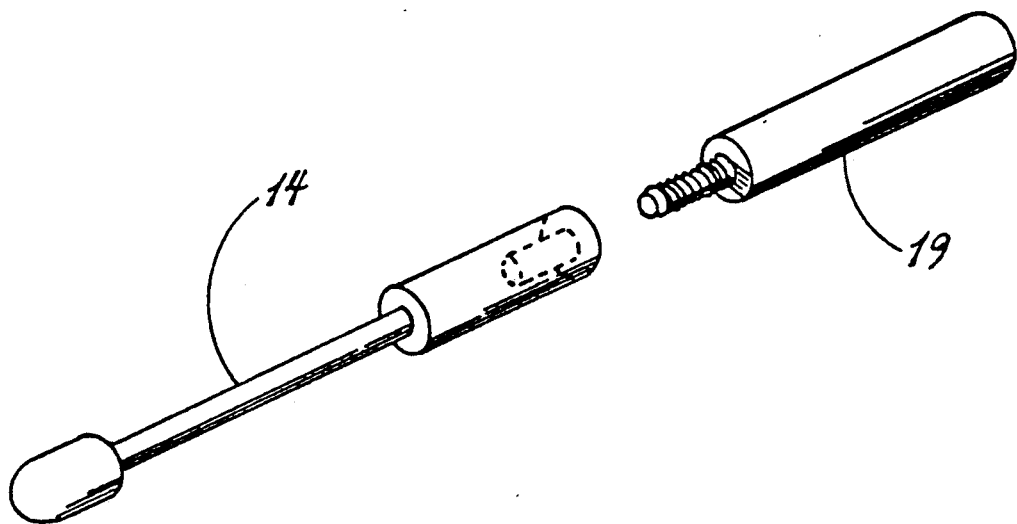
FIG. 8 shows a perspective view of one embodiment of the surgical instrument wherein the shaft portion of the instrument comprises a removable handle.

FIG. 8 shows still another alternative embodiment wherein the shaft portion adjacent to the second end of the instrument is removable from the remainder of the instrument and so comprises a removable handle 19. This may be accomplished by the use of a threaded connection or any other means for removing and reattaching. This may be useful for applications wherein a single handle may be provided for use with various types of instruments including the surgical instrument of the present invention.

Figure 9:
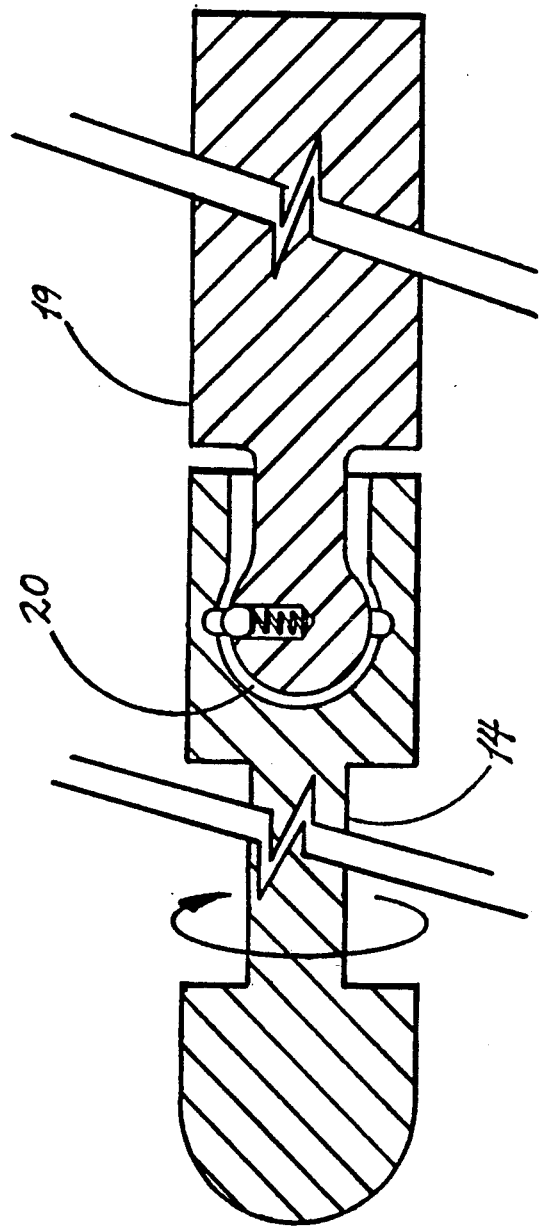
FIG. 9 shows a longitudinal cross section of one embodiment of the surgical instrument wherein the shaft portion and the reduced diameter portion incorporate mating means for rotating so that the two portions are rotatable relative to each other.

FIG. 9 shows a longitudinal cross section of still another alternative embodiment wherein the shaft portion or handle 19 adjacent to the second end of the instrument and the reduced diameter portion 14 of the instrument incorporate mating rotating means such as the ball and socket joint 20 shown. The shaft portion or handle 19 may or may not be made to be removable from the reduced diameter portion 14 at the mating rotating means 20. This embodiment allows the reduced diameter portion of the instrument to be separately rotated from the shaft portion of the instrument. This may be useful for applications wherein it is desired to unroll the prosthetic sheet repair material from the reduced diameter portion of the instrument while the shaft portion or handle 19 is held stationary.

The surgical instrument of the present invention may be made of any suitable material that possesses adequate rigidity, is biocompatible, easily cleaned and is sterilizable. Stainless steels suitable for surgical instruments are preferred.

The surgical instrument is intended for use primarily with GORE-TEX ®Surgical Membrane (W. L. Gore & Associates, Inc; Flagstaff, AZ) or the thicker GORE-TEX ®Soft Tissue Patch material (W. L. Gore & Associates, Inc; Flagstaff, AZ) which is intended primarily for reconstruction of hernias. Both of these products are comprised of porous polytetrafluoroethylene. This material has almost no memory, so that when it is rolled-up around the reduced diameter of the inventive surgical instrument it has almost no tendency toward unrolling. Conversely, when unrolled from the instrument at a surgical site requiring repair, it displays almost no tendency to want to resume its rolled-up form.

The inventive surgical instrument is typically used as follows. A laparoscopy incision is made convenient to the defect site. A suitable trocar sleeve is then inserted into the incision. A piece of prosthetic repair material of a suitable type is cut to the necessary shape, rolled-up around the reduced diameter portion of the instrument, and delivered to the defect site through the bore of the trocar sleeve. The surgical instrument is then rotated in such a way as to unroll the prosthetic sheet repair material and present it in flat form to the defect site. Forceps, introduced via another trocar sleeve, may be used to unroll or aid in unrolling the prosthetic repair material from the surgical instrument. The tip of the surgical instrument and the forceps may subsequently be used to position the prosthetic repair material as required over the defect site. The repair material may then be attached to the defect site by any suitable means for surgical fastening. The procedure may be viewed as necessary with a suitable laparoscope.

EXAMPLE

The abdomen of a female, foxhound-cross dog was implanted with a GORE-TEX Surgical Membrane, using only laparoscopy. A standard 10 mm trocar sleeve was emplaced near the abdominal midline via a 2 cm long incision. A standard 5 mm trocar sleeve was emplaced at the right lateral abdominal sidewall via a second incision. A 10 mm operating laparoscope was introduced through the 10 mm sleve. A 3×3 cm GORE-TEX Surgical Membrane was wrapped around a surgical instrument of the present invention. The instrument, made of stainless steel, was of 57 cm length, 5 mm outside diameter, with a reduced length segment of 3 mm diameter and 8.5 mm length beginning 10 mm from the end of the instrument. The instrument was then introduced to the abdominal cavity through the operating channel of the laparoscope. An atraumatic forceps, passed through the 5 mm sleeve, was used to grasp the GORE-TEX Surgical Membrane and unwrap it. The forceps was then used to place the Surgical Membrane along the left abdominal sidewall.

A specially designed "tack gun" loaded with a single stainless steel barbed tack similar to those described in U.S. Pat. No. 4,873,976 was introduced through the 5 mm sleeve. A tack was then placed into the abdominal wall, through the GORE-TEX Surgical Membrane, securely fastening the surgical membrane to the abdominal wall. Three tacks were thus used to implant the GORE-TEX Surgical Membrane. The GORE-TEX Surgical Membrane became slightly wrinkled as tension was not applied to the repair material with the forceps during placement of the tacks. It appeared that wrinkling would be avoided by the use of tension via forceps.

Twenty-four days post operatively, the animal was euthanized. The implant site was removed and preserved in formalin. The prosthetic repair material remained wrinkled, but the tacks were in place and had held the GORE-TEX Surgical Membrane. No adverse tissue reaction could be seen grossly at the GORE-TEX Surgical Membrane site.

We claim:

1. A process of implanting a prosthetic sheet repair material comprising:
   a) making a surgical incision in a body;
   b) inserting a hollow sleeve into the body through incision;
   c) providing a surgical laparoscopy instrument comprising a rod having a length, an outside diameter and first and second ends, further having a portion of said length adjacent to the first end wherein said length portion has the reduced outside diameter in comparison to the rod outside diameter;
   d) rolling a substantially flat sheet of prosthetic sheet repair material around the reduced diameter portion of the surgical laparoscopy instrument;
   e) inserting said laparoscopy instrument and prosthetic sheet repair material into the incision through the hollow sleeve;
   f) unrolling the sheet of prosthetic repair material from the surgical laparoscopy instrument;
   g) fastening the sheet of prosthetic repair material within the body by means for surgical fastening;
   h) removing the laparoscopy instrument and the hollow sleeve from the body; and
   i) closing the incision.

2. A process according to claim 1 wherein the providing step comprises providing the surgical laparoscopy instrument comprised of stainless steel.

3. A process according to claim 1 wherein the providing step comprises providing the length portion of surgical laparoscopy instrument with a slot through the reduced diameter.

4. A process according to claim 3 wherein the providing step comprises providing the surgical laparoscopy instrument comprised of stainless steel.

5. A process according to claim 1 wherein the providing step comprises providing at least a part of the length of the surgical laparoscopy instrument adjacent to the second end with a flexible shaft.

6. A process according of claim 1 wherein the providing step comprises providing at least a part of the length of the surgical laparoscopy instrument removable from the length portion having the reduced outside diameter and comprising a removable handle.

7. A process according to claim 6 wherein the providing step comprises providing the first end of the surgical laparoscopy instrument connected to the second end by a mating means for rotating whereby the first end may be rotated relative to the second end.

8. A process according to claim 1 wherein the providing step comprises providing the first end of the surgical laparoscopy instrument connected to the second end by a mating means for rotating whereby the first end may be rotated relative to the second end.

* * * * *